United States Patent [19]

Gizurarson et al.

[11] Patent Number: 5,942,237
[45] Date of Patent: *Aug. 24, 1999

[54] PHARMACEUTICAL PREPARATION FOR TOPICAL ADMINISTRATION OF ANTIGENS AND/OR VACCINES TO MAMMALS VIA A MUCOSAL MEMBRANE

[75] Inventors: Sveinbjorn Gizurarson, Reykjavik, Iceland; Iver Heron, Jyderup, Denmark

[73] Assignee: Lyfjathroun H.F., Reykjavik, Iceland

[*] Notice: This patent issued on a continued prosecution application filed under 37 CFR 1.53(d), and is subject to the twenty year patent term provisions of 35 U.S.C. 154(a)(2).

[21] Appl. No.: 08/501,112
[22] PCT Filed: Feb. 14, 1994
[86] PCT No.: PCT/DK94/00062
    § 371 Date: Oct. 6, 1995
    § 102(e) Date: Oct. 6, 1995
[87] PCT Pub. No.: WO94/17827
    PCT Pub. Date: Aug. 18, 1994

[30] Foreign Application Priority Data

Feb. 15, 1993 [DK] Denmark ................... 0170/93

[51] Int. Cl.⁶ ............. A61K 39/39; A61K 9/10; A61K 9/113; A61K 9/06
[52] U.S. Cl. ................ 424/278.1; 424/234.1; 424/184.1; 424/280.1; 424/283.1; 568/623; 536/115; 554/1; 562/606; 436/71
[58] Field of Search ............ 424/234.1, 278.1, 424/184.1, 280.1, 283.1; 568/623; 536/115; 554/1; 562/606; 436/71

[56] References Cited

U.S. PATENT DOCUMENTS 4,315,925  2/1982  Hussain et al. .
4,985,242  1/1991  Sekine et al. .

FOREIGN PATENT DOCUMENTS

| 0440289 | 8/1991 | European Pat. Off. . |
|---|---|---|
| 0 534 618 A2 | 3/1993 | European Pat. Off. . |
| 0544612 | 6/1993 | European Pat. Off. . |
| 1960714 | 5/1975 | Germany . |
| 3446515 | 6/1986 | Germany . |
| 3911442 | 11/1989 | Germany . |
| 1171125 | 11/1969 | United Kingdom . |
| 9203162 | 3/1992 | WIPO . |
| WO 92/18147 | 10/1992 | WIPO . |

OTHER PUBLICATIONS

Sveinbjorn Gizurarson (1990) Acta Pharm. Nord. 2(2), 105–122. "Animal models for intranasal drug delivery studies".

Two abstract pages, Abstracts 27347n —27367u, *Chemical Abstracts*, 106:13–14 (1987).

Primary Examiner—Anthony C. Caputa
Assistant Examiner—Khalid Masood
Attorney, Agent, or Firm—Merchant, Gould, Smith, Edell, Welter & Schmidt P.A.

[57] ABSTRACT

A novel type of formulation for the topical administration of antigens and/or vaccines to mammals via mucosal membranes comprising one or more adjuvants/vehicles selected from (a) polyoxyethylene sorbitan monoesters, (b) polyoxyethylene castor oil, (c) caprylic/capric acid glycerides and (d) gangliosides in an amount of 0.01 to 15% (v/v) calculated on the total volume of the preparation. This formulation enhances the immunological response n a mammal following mucosal administration, e.g. nasal, oral, rectal or vaginal application.

20 Claims, 1 Drawing Sheet

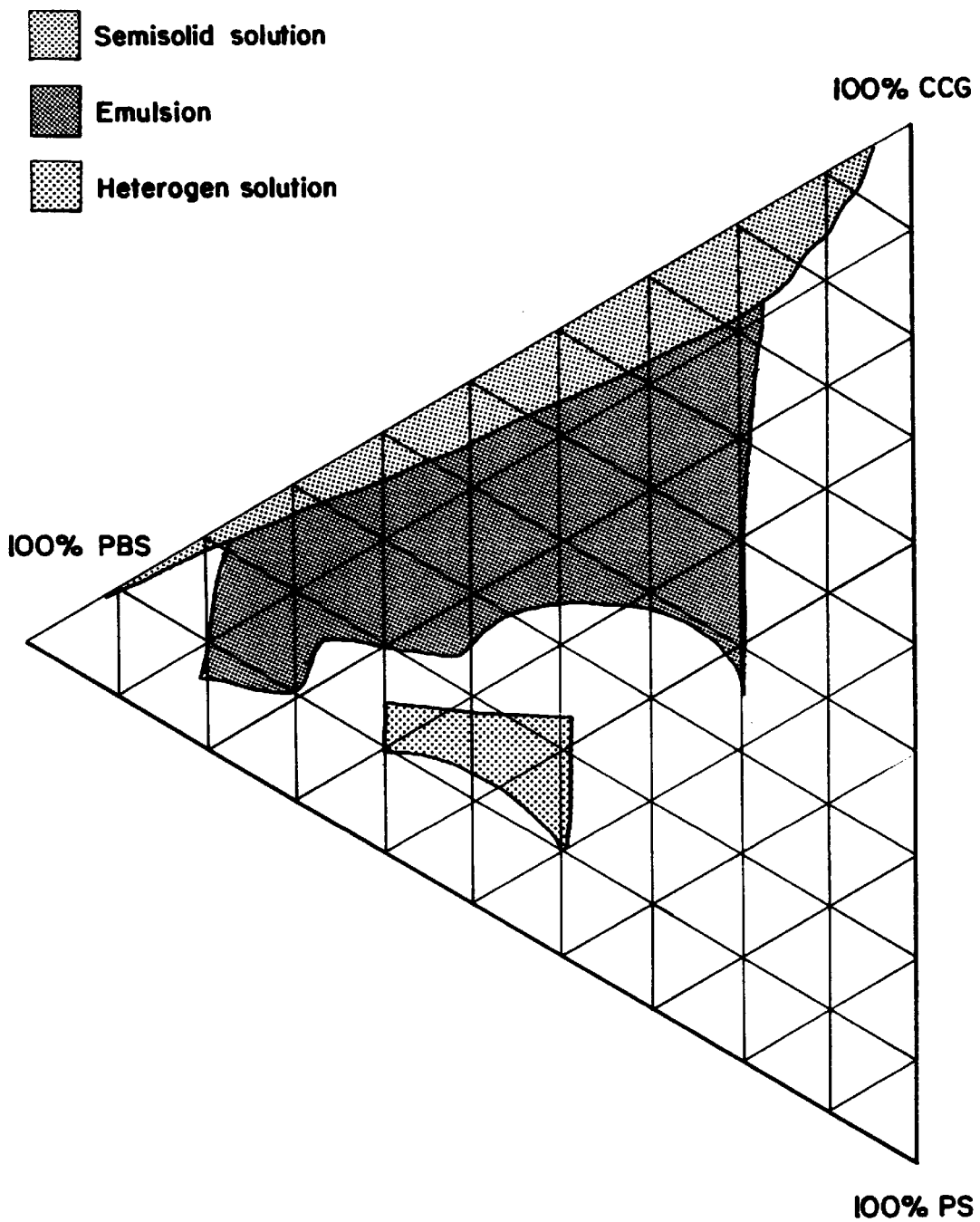

PHARMACEUTICAL PREPARATION FOR TOPICAL ADMINISTRATION OF ANTIGENS AND/OR VACCINES TO MAMMALS VIA A MUCOSAL MEMBRANE

This application is a 371 of PCT/DK94/00062 filed Feb. 14, 1994 which claims priority from Denmark application 0170/93 filed Feb. 15, 1993.

The present invention relates to novel pharmaceutical preparations for topical administration of antigens and/or vaccines to mammals, including humans, via a mucosal membrane. The invention also relates to the use of certain compounds (to be defined in more detail below) as adjuvants or vehicles in such preparations.

The parenteral (intramuscular and subcutaneous) administration of antigens and/or vaccines is normally regarded as the most convenient way of administration. However, the administration by injection presents a range of disadvantages. Thus it requires the use of sterile syringes and may cause pains and irritations, particularly in the case of repeated injections, including the risk of infection. More significantly, in the case of intramuscular injections there is also a risk of the infection being poorly tolerated. There is likely to be an induration (hardening of tissue), haemorrhage (bleeding) and/or necrosis (local death of tissue) at the injection site. Besides, injections cannot be administered satisfactorily by untrained persons.

Administration of attenuated virus, bacteria or parasites has been attempted intranasally as well as through other mucosal surfaces. The elicitation of an immune response by such antigens through mucosal surfaces cannot be considered unexpected in such cases, because the modified live pathogens of the vaccine is following the natural route of infection of the wild-type pathogen creating immunity through a sub-clinical infection. The use of modified live pathogen to effect immunization entails a certain risk, however, because the more purified antigens are very poor immunogens and thus require effective formulations and adjuvants to produce a clinically protective immune response.

Mucosal administration is currently receiving special interest, attempting to stimulate locally produced antibodies (secretory IgA antibodies) and also to avoid the inconveniences caused by the direct intervention into the organism in connection with parenteral administration. Additionally, this route of administration may conveniently be used as an alternative to parenteral injection, since it may well be performed by an untrained person. Furthermore, small children will avoid the psychological irritation during injection (vaccination).

In order to be an attractive alternative to parenteral administration, the intranasal administration should be capable of stimulating humoral and cellular immune factors both systemically (mainly of the IgG isotype) and at mucosal surfaces where most pathogens enter the host by locally produced antibodies of the secretory IgA ($IgA_s$) isotype. Several oral vaccines have been shown to induce appropriate $IgA_s$ responses in remote secretions including saliva, lachrymal fluid and fluids obtained from nasal and gastrointestinal washes. Such intranasally administered vaccines and/or antigens may not cause any considerable pain or irritation to the patient nor any irreversible damage or irritation to the mucosal surfaces.

In nasal administration, the antigen and/or vaccine must be applied to the mucosa in such a condition that it is able to penetrate or to be absorbed through the mucosa. In order to penetrate the mucus the vehicle must be biocompatible with the mucus and hence have a certain degree of hydrophilicity.

Vaccines and/or antigens are not able to be administered in pure form. It is necessary to blend them with other components to obtain a preparation which is ready for use. Dependent on the chemical properties of the antigen and/or vaccine it will be necessary to take various considerations into account before a pharmaceutical preparation for humans or animals can be produced.

BRIEF DESCRIPTION OF THE DRAWINGS

FIG. 1 illustrates a phase diagram of a composition according to the present invention.

It has now surprisingly been found that the topical administration of antigens and/or vaccines to mammals via mucosal membranes can be performed in a new and significantly improved manner by using a novel type of formulation, said preparation being characterized by comprising one or more adjuvants/vehicles selected from (a) polyoxyethylene sorbitan monoesters of the general formula

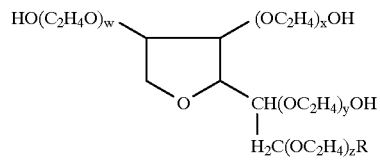

wherein R is selected among laurate, palmitate, stearate and oleate, and wherein the sum of w, x, y and z is 4, 5 or 20;

(b) polyoxyethylene castor oil produced by reacting 1 mole of castor oil or hydrogenerated castor oil with 10–45 moles of ethylene oxide;

(c) caprylic/capric acid glycerides of the general formula

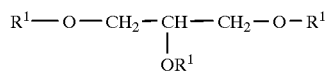

wherein each $R^1$ independently is H or a $C_8$–$C_{10}$ acyl group containing 1–6% free glycerol, 45–50% monoglycerides, 30–40% diglycerides and 5–9% triglycerides, and (d) gangliosides of the general formula

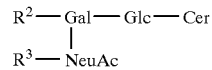

wherein Gal is galactose, Glc is glucose, Cer is ceramide (N-fatty acyl sphingosine) and NeuAc is N-acetyl neuraminic acid (sialic acid), and wherein $R^2$ may be one or more substances selected among N-acetyl galactosamine, galactose, N-acetyl neuraminic acid or combinations thereof, and $R^3$ is H or N-acetyl neuraminic acid in an amount of 0.01 to 15% (v/v) calculated on the total volume of the preparation.

The nasal epithelial membrane consists of practically a single layer of epithelial cells (pseudostratified epithelium) and it is therefore even more suited for antigen and/or vaccine administration than other mucosal surfaces having squamous epithelial layers, such as the mouth, vagina, etc. These surfaces, however, are also well suited for the application of antigens and/or vaccines with the delivery system according to the invention. The extensive network of blood capillaries under the nasal mucosa is—together with the high density of T and B cells—particularly suited to provide a rapid recognition of the antigen and/or the vaccine, which may also provide a quick immunological response.

For liquid compositions it is essential that the effective amount of the antigen and/or the vaccine can be administered in a volume of less than about 300 μl for human subjects. A larger volume can be disagreeable to the patient and will evidently drain out anteriorly through the nostrils or posteriorly toward the pharynx. The result is that a part of the antigen and/or the vaccine is lost from the absorption site.

The volume is preferably from about 20 μl to about 125 μl and preferably administered into both nostrils.

A variety of vehicle systems for the delivery of antigens and/or vaccines have been developed. The literature to date has suggested that uptake of antigens and/or vaccines from the nasal mucosa is frequently made possible by incorporation of a special vehicle system into the formulation, adding certain amount of absorption enhancing agents or a certain amount of adjuvants.

Much has been written regarding the potential use of various vehicles as drug delivery systems for intranasal administration. In such vehicle systems, the medicament is rapidly absorbed into the blood stream. One of the problems encountered in using such vehicle systems is that the antigen and/or the vaccine is absorbed and degraded without recognition and, therefore, without stimulating an immunological response. The system according to the invention describes a vaccine/antigen delivery system which provides a clear immunological response in spite of the short contact time inside the nasal cavity.

A possible enhancement of the immunological response after mucosal administration of polyoxyethyl-35-castor oil, caprylic/capric acid glycerides and/or gangliosides together with an antigen or a vaccine has not been suggested anywhere in the prior art.

U.S. Pat. No. 4,610,868 describes a lipid matrix carrier for parenteral administration of drugs. This system requires a lipid matrix carrier comprising a hydrophobic compound, an amphipathic compound and a bioactive agent with a globular structure of a diameter between 500 and 100,000 nm. Here the hydrophobic compound may comprise a mixture of glycerides and the amphipathic compound may comprise a sphingolipid. Furthermore, this formulation may be administered into the nasal area. However, this system is not acceptable as a nasal formulation, due to the rapid clearance inside the nose and the large globular structure. Therefore, this system will be transferred into the stomach by the cilia before the bioactive agent is released.

U.S. Pat. No. 4,985,242 describes an intranasally applicable powdery pharmaceutical composition comprising a polypeptide with physiological activity, a quaternary ammonium compound, and a lower alkyl ether of cellulose. Typical surfactants in this composition are polyoxyethylene sorbitan fatty acid esters. This powdery pharmaceutical composition is stated to have an excellent preservability and chemical stability of the polypeptides. Further, when the composition is administered to the nasal cavity in the form of a spray, the polypeptides are absorbed effectively through the nasal mucosa. However, the surfactant concentration is critical since, on the one hand, high concentrations lead to sticky preparations without powder characteristics. On the other hand, low concentrations will not enable the induction of an immunological response. If the purpsose of U.S. Pat. No. 4,985,242 had been to induce an immunological response, which is not the case, this would be regarded as a serious drawback when protein and peptide drugs were to be administered. These surfactants would therefore not be usable for the purpose of the present invention.

Several other references relating to the use of a polyoxyethylene derivative of a sorbitan ester in nasal preparations are known. However, no reference describes the substance according to the invention as an adjuvant or as an immunomodulator. This effect is indeed surprising and unexpected. A novel method of administering the natural female sex hormones 17β-oestradiol and progesterone as solutions, suspensions, gels and ointments, containing 1% to 2% Tween 80, is described in U.S. Pat. No. 4,315,925. From EP Patent No. 246,625 is known an aqueous steroid formulation for nasal administration of an anti-inflammatoric steroid preparation containing propylene glycol, polyethylene glycol 400 and 1% to 4% Tween 20. EP Patent No. 242,643 describes an intranasal administration of drugs, especially insulin, using e.g. 0.01% to 0.5% Tween 80 to reduce the nasal irritation by other absorption promoters. Finally, in PCT/AT87/00015 a sprayable, Tween-containing formulation for e.g. benzodiazepines is described. However, this formulation requires the use of a propeller gas.

The present invention presents a new and significantly improved method for the administration of antigens/vaccines, using the above new type of formulation. The method provides protective immune response in recipients of the antigen and/or the vaccine, both systemically and locally, which are elicited after intranasal immunization.

The primary object of the invention is to provide an intranasal composition, which is capable of producing a high systemic immune response (humoral and cellular, mainly of the IgG isotype) as well as locally produced antibodies of the secretory IgA isotype at mucosal surfaces without causing unacceptable damage to the nasal epithelial membrane.

It is another object of the invention to provide a controlled delivery system for intranasal application, which is biocompatible with the mucus and which is capable of dissolving required amounts of antigens and/or vaccines in small volumes.

According to an aspect of the invention the present delivery system is also usable for other mammalian surfaces such as the vagina, eye, mouth, lungs, ear, genital tract, gastrointestinal tract, rectum, skin etc.

As mentioned previously, the pharmaceutical preparation of the present invention is characterized by comprising one or more substances selected from (a) polyoxyethylene sorbitan monoesters, (b) polyoxyethylene glycerol triesters, (c) caprylic/capric acid glycerides, and (d) gangliosides.

The preferred polyoxyethylene sorbitan monoester (a) is Polysorbate 20, which is a laurate ester of sorbitol and its anhydrides copolymerized with approximately 20 moles of ethylene oxide for each mole of sorbitol and sorbitol anhydrides.

The polyoxyethylene glycol triester (b) is preferably Polyoxyl-35-castor oil. This compound is mainly the triricinoleate ester of ethoxylated (about 35 moles) glycerol with smaller amounts of polyethylene glycol ricinoleate and the corresponding free glycols. Polyoxyl-35-castor oil is commonly known as Cremophor EL.

The caprylic/capric acid glycerides (c) are principally a mixture of mono-, di- and triglycerides in which the acid groups are only caprylic and capric acid groups. They are known commercially under the trade name Imwitor.

The gangliosides (d) of the above formula IV are principally a mixture of asialo-, monosialo-, disialo- and trisialo-gangliosides.

The composition according to the invention may comprise one or more additional pharmaceutical excipients, selected among surfactants and absorption promoters, such as polyoxyethylene alcohol ethers, bile salts and derivatives thereof, fusidic acid and derivatives thereof, oleic acid, lecithin, lysolecitines, Tween 21 to 85, etc, water absorbing polymers, such as glycofurol, polyethylene glycol 200 to 7500, polyvinylpyrrolidone, propylene glycol or polyacrylic acid, gelatine, cellulose and derivatives, etc.; substances which inhibit enzymatic degradation, such as aprotinin, etc.; alcohols, such as ethanol, glycerol, benzyl alcohol, etc.; organic solvents such as ethyl acetate, benzyl alcohol, etc.; hydrophobic agents, such as vegetable oil, soybean oil, peanut oil, coconut oil, maize oil, olive oil, sunflower oil, "Miglyols" or mixtures thereof, etc.; pH-controlling agents, such as nitric acid, phosphoric acid, acetic acid, citrates, etc.; preservatives and osmotic pressure controlling agents, such as glycerol, sodium chloride, methyl paraoxybenzoate, benzoic acid, etc.; liposome and/or emulsion formulations, such as lecitines, etc.; microencapsulated formulations; propellants, such as butane; water etc. The use of propellants is not compulsory in the preparation according to the invention.

The pharmaceutical preparation of the invention may comprise any antigens and/or vaccines. The vaccines may be selected among all the vaccines causing diseases in humans or animals. These include bacterial vaccines such as chlamydia, cholera, diphtheria, haemophilus influenzae, leprosy, meningococcal, pertussis, pneumococcal, shigella, tetanus, tuberculosis, etc.; virus vaccines such as hepatitis viruses, herpes viruses, human immunodeficiency viruses (HIV), influenza viruses, measles virus, mumps virus, parainfluenza virus, paramyxo viruses, polio virus, rabies viruses, respiratory syncytial viruses, rhinovirus types, rotavirus, rubella virus, etc., and parasite vaccines such as vaccines for leishamaniasis, schistosomiasis and trypanosomiasis, which may be used to produce local and/or systemic antibodies.

The invention is described in further detail in the following examples.

EXAMPLE I

A tetanus vaccine formulation consists of (a) tetanus toxoid (22.5 µl), gangliosides (10.0 µl) and Tween-20 (7.5 µl); (b) tetanus toxoid (22.5 µl) and a solution of an Imwitor/cremophor mixture (1:1) (17.5 µl); (c) tetanus toxoid (22.5 µl) and isotonic saline (17.5 µl). Formulations a, b and c are administered intranasally to mice (2.5 µl/nostril) under i.p. nembutal anaesthesia. Each mouse received 1.5 Lf tetanus toxoid. Three weeks later the mice are boosted with the same formulations and one week after, they are sacrificed and serum and nasal wash antibodies are measured. The excess serum samples are furthermore measured in living animals receiving live tetanus toxoid in the neutralisation test. The following results were obtained:

| Formulation | Blood IgG | Nasal IgA | Neutralisation |
| --- | --- | --- | --- |
| Control (s.c.)[a] | 1.09 | 105 | 0.5 |
| Formulation a | 2.45 | 625 | 0.5 |
| Formulation b | 1.54 | 1132 | 0.8 |
| Formulation C | 0.0007 | 30 | 0.000 |

[a] Commercially available product, single administration.

EXAMPLE II

A diphtheria vaccine formulation consists of (a) diphtheria toxoid (7.5 µl), gangliosides (12.5 µl) and Tween-20 (20.0 µl); (b) diphtheria toxoid (7.5 µl), PBS-saline (12.5 µl) and a solution of an Imwitor/cremophor mixture (1:1) (20.0 µl); (c) diphtheria toxoid (7.5 µl) and isotonic saline (32.5 µl). Formulations a, b and c are administered intranasally to mice (2.5 µl/nostril) under i.p. nembutal anaesthesia. Each mouse received 1.5 Lf diphtheria toxoid. Three weeks later the mice are boosted with the same formulations and one week after they are sacrificed and serum and nasal wash antibodies are measured. The excess serum samples are furthermore measured in the neutralisation test. The following results were obtained:

| Formulation | Blood IgG | Nasal IgA | Neutralisation |
| --- | --- | --- | --- |
| Control (s.c.)[a] | 0.354 | 34 | 0.012 |
| Formulation a | 0.004 | 36 | 0.025 |
| Formulation b | 2.22 | 352 | 0.020 |
| Formulation c | 0.0004 | 30 | 0.000 |

[a] Commercially available product, single administration.

EXAMPLE III

An influenza vaccine formulation consists of (a) influenza virus vaccine (5.0 µl), gangliosides (10.0 µl), a solution of an Imwitor/cremophor mixture (1:1) (6.0 µl), distilled water (16.5 µl) and a PBS solution (2.5 µl); (b) influenza virus vaccine (5.0 µl) and isotonic saline (35.0 µl). The formulation was administered intranasally to mice (2.5 µl/nostril) under i.p. nembutal anaesthesia. Each mouse received 0.2 µg influenza HA. Four weeks later the mice were sacrificed and the serum HI titer measured. The following results were obtained:

| Formulation | HI test |
| --- | --- |
| Control (s.c.)[a] | 1/80 |
| Formulation a | 1/160 |
| Formulation b | 1/20 |

[a] Commercially available product.

EXAMPLE IV

A tetanus and diphtheria vaccine formulation consists of (a) tetanus toxoid (510 µl), diphtheria toxoid (169 µl), gangliosides (75 µl) and Tween-20 (750 µl); (b) tetanus toxoid (510 µl), diphtheria toxoid (169 µl) and a solution of an Imwitor/cremophor mixture (1:1) (220 µl). Six rabbits were divided into 3 groups of 2 rabbits each (4 nostrils in each group). Formulations a and b were administered intranasally (50 µl into each nostril) under unanaesthesized condition. Each rabbit received 18 Lf tetanus toxoid and 18 Lf diphtheria toxoid. The last group served as control and received only a single intranasal dose of isotonic saline. The rabbits were sacrificed by intravenous injection of pentobarbital 3½ after dosing. Each nasal cavity was opened and individually evaluated macroscopically. The evaluator was blind as to the dosing scheme. The data show that the lesions observed were distributed almost evenly over the control and the test groups. Small focal nature and anterior location of some lesions were obtained, corresponding to the abrasion from the tip of the applicatior pipette. No macroscopic difference was observed between isotonic saline and the formulations a and b.

EXAMPLE V

Three solvents, phosphate buffered saline (PBS), caprylic/capric acid glycerides (CCG) and polyoxyethylene sorbitan monoesters (PS), were mixed together in various concentrations in order to see their interrelationship (phase diagram). The figure shows that within certain concentration rages an emulsion or a semisolid solution is achieved. CCG and PBS show a heteogeneous solution upon mixing when little or no PS is present in the system. Viscosity, bioadhesiveness, sprayability and homogenicity (in the case of an emulsion delivery system) may be controlled, dependent on the concentration of each substance.

EXAMPLE VI

A tetanus vaccine formulation consists of (a) tetanus toxoid (510 μl), gangliosides (75 μl), polyoxyethylene sorbitan monoesters (750 μl) and saline (169 μl); (b) commercially available tetanus/diphteria vaccine, adsorbed to aluminum hydroxide. Formulation a was administered intranasally to rabbits (50 μl/nostril) using no anaesthesia nor sedation, and formulation b was administered subcutaneously. Each rabbit received 18 Lf tetanus toxoid and 18 Lf diphtheria toxoid. Three weeks later the rabbits received a booster of the same formulations. Weekly serum samples were collected from the marginal ear vein, and the samples were measured using the ToBi technique. The following results were obtained (IU/ml):

| Formulation | 2 weeks | 3 weeks | 4 weeks |
|---|---|---|---|
| a | 0.034 | 1.012 | 0.847 |
| b | 0.477 | 1.572 | 1.456 |

EXAMPLE VII

The synergistic effect between caprylic/capric acid glycerides (CCG) and polyoxyethylene sorbitan monoesters (PS) was determined as follows:

Six diphtheria (1.5 Lf) vaccine formulations were made: (a) in phosphate buffered saline (PBS); (b) commercially available $Al(OH)_3$ adsorbed vaccine for subcutaneous injection; (c) in PBS solution containing 40% polysorbate 20; (d) in PBS solution containing 40% polysorbate 20 and 25% polyoxyethylene castor oil; (e) in 40% polysorbate 20 and 10% caprylic/capric acid glyceride (mono- and di-glycerides); and (f) in 40% polysorbate 20, 25% polyoxyethylene castor oil and 10% caprylic/capric acid glyceride (mono- and di-glycerides). The formulations were administered intranasally to mice (2.5 μl/nostril) under i.p. nembutal anaesthesia. Three weeks later the mice received a booster containing the same formulations, and a further week later they were sacrified and serum antibodies were measured. The following results were obtained:

| Formulations | Diphth. IgG |
|---|---|
| a | 0.0004 |
| b | 0.354 |
| c | 0.448 |
| d | 0.127 |
| e | 7.3 |
| f | 0.115 |

It appears that neither PS nor CCG alone can provide a satisfactory effect. This is only the case with combinations of PS and CCG.

EXAMPLE VIII

In this example the synergistic effect between caprylic/capric acid glycerides (CCG) and polyoxyethylene sorbitan monoesters (PS) was investigated further.

Seven influenza A vaccine formulations were made: (a) in phosphate buffered saline (PBS); (b) in PBS solution containing 25% polyoxyethylene castor oil; (c) in PBS solution containing 25% polyoxyethylene castor oil and 10% caprylic/capric acid glyceride (mono- and di-glycerides); (d) in PBS solution containing 40% polysorbate 20; (e) in PBS solution containing 40% polysorbate 20 and 25% polyoxyethylene castor oil; (f) in 40% polysorbate 20 and 10% caprylic/capric acid glyceride (mono- and di-glycerides); and (g) in 40% polysorbate 20, 25% polyoxyethylene castor oil and 10% caprylic/capric glyceride (mono- and di-glycerides). The formulations were administered intranasally to mice (2.5 μl/nostril) under i.p. nembutal anaesthesia. Three weeks later the mice received a booster, containing the same formulations, and a further week later they were sacrificed and the serum antibodies were measured. The following results were obtained:

| Formulation | IgG |
|---|---|
| a | 0.072 |
| b | 0.053 |
| c | 0.073 |
| d | 0.114 |
| e | 0.038 |
| f | 0.354 |
| g | 0.037 |

Caprylic/capric acid glycerides were not tested alone, since they are insoluble in water.

EXAMPLE IX

This example illustrates the selection of the optimal CCG and PS concentration.

Seven diphtheria vaccine formulations were made: (a) in phosphate buffered saline (PBS); (b) in PBS solution containing 35% polysorbate 20; (c) in PBS solution containing 57.5% polysorbate 20; (d) in PBS solution containing 35% polysorbate 20 and 10% caprylic/capric acid glyceride (mono- and di-glycerides); (e) in PBS solution containing 57.5% polysorbate 20 and 10% caprylic/capric acid glyceride (mono- and di-glycerides); (f) in PBS solution containing 35% polysorbate 20 and 24% caprylic/capric acid glyceride (mono- and di-glycerides); and (g) in 57.5% polysorbate 20 and 24% caprylic/capric acid glyceride (mono- and di-glycerides). The formulations were administered intranasally to mice (2.5 μl/nostril) under i.p. nembutal anaesthesia. Three weeks later the mice received a booster, containing the same formulations, and one further week later they were sacrificed and the serum antibodies were measured. The following results were obtained:

| Formulation | IgG |
|---|---|
| a | 0.365 |
| b | 1.22 |
| c | 0.092 |
| d | −9.65 |
| e | −2.33 |
| f | 1.31 |
| g | −26.6 |

Caprylic/capric acid glycerides were not tested alone, since they are insoluble in water.

EXAMPLE X

The selection of the optimal CCG and PS concentration is further illustrated in this example.

Seven diphtheria and tetanus vaccine formulations were made by using fixed caprylic/capric acid glyceride (mono- and di-glycerides) concentration (10%) but variable polysorbate 20 (mono-ester) concentration, ranging from 28% (a) with 2% increments up to 40% (g). The formulations were administered intranasally to mice (2.5 μl/nostril) under i.p. nembutal anaesthesia. Three weeks later the mice received a booster, containing the same formulations, and one additional week later they were sacrificed and the serum antibodies were measured. The following results were obtained:

| Formulation | Diphth. IgG | Tetan. IgG |
|---|---|---|
| a | 0.07 | 0.04 |
| b | 0.17 | 0.04 |
| c | 0.10 | 0.02 |
| d | 0.16 | 0.03 |
| e | 1.60 | 0.01 |
| f | 1.25 | 0.06 |
| g | 0.27 | 0.004 |

EXAMPLE XI

This example concerns the selection of polyoxyethylene fatty acid esters. Such polyoxyethylene fatty acid esters are found as mono- and trimesters. Diphtheria toxoids were formulated in the following different compositions: (a) in isotonic phosphate buffered saline (PBS); (b) in PBS solution containing 47% polysorbate 80 (tri-ester); and (c) in PBS solution containing 47% polysorbate 20 (mono-ester). The formulations were administered intranasally to mice (2.5 μl/nostril) under i.p. nembutal anaesthesia. Four weeks later the mice were sacrificed and the serum antibodies were measured. The following results were obtained:

| Formulation | IgG |
|---|---|
| a | 0.001 |
| b | 0.002 |
| c | 0.006 |

EXAMPLE XII

The selection of glyceride esters was performed as follows: Six tetanus (1.5 Lf) and diphtheria (1.5 Lf) vaccine formulations were made. The formulations were administered intranasally to mice (2.5 μl/nostril) under i.p. nembutal anaesthesia. Four weeks later the mice were sacrificed and serum and nasal wash antibodies were measured. The following results were obtained:

| Formulation | Diphth. IgG | Tetan. IgG |
|---|---|---|
| Negative control | 0.0013 | 0.0078 |
| $C_{8 \text{ and } 10}$ diglyceride ester (Miglyol 829) (3.5%) | 0.0003 | 0.0030 |
| $C_{8 \text{ and } 10}$ mono-diglyceride ester (Imwitor 742) (7%) | 0.0027 | 0.2580 |
| $C_{16}$ triglyceride ester (Dynasan 116) (2.5%) | 0.0014 | 0.0057 |

We claim:

1. A pharmaceutical preparation for topical administration of antigens, vaccines, or both to mammals via a mucosal membrane, the preparation consisting essentially /of:
   (a) a polyoxyethylene sorbitan monoester (PS) of the general formula:

$$HO(C_2H_4O)_w \quad (OC_2H_4)_xOH$$
$$CH(OC_2H_4)_yOH$$
$$H_2C(OC_2H_4)_zR$$

wherein R is laureate, palmitate, stearate or oleate; and each of w, x, y and z is independently 1 or 2; or each of w, x, y, z is independently less than or equal to 17 and the sum of w, x, y and z is 20;
   (b) a mixture of mono-, di-, and triglycerides of a caprylic acid, a capric acid, or both (CCG) having the general formula:

$$R^1 - O - CH_2 - CH - CH_2 - O - R^1$$
$$OR^1$$

wherein each $R^1$ independently is H or a $C_8$–$C_{10}$ acyl group, provided that at least one $R^1$ is a $C_8$–$C_{10}$ acyl group; and
   (c) water, an aqueous buffer, an antigen, or a combination thereof;
      wherein, the CCG and PS are present at respective concentrations of 0.01% to 24% CCG and 0.1% PS to 57.5% PS, each percentage being (v/v) and the preparation containing more PS than CCG and more water or aqueous buffer than oil.

2. A pharmaceutical preparation according to claim 1, wherein the mixture of mono-, di-, and triglycerides of a caprylic acid, a capric acid or both comprises 1–6% free glycerol, 45–50% monoglycerides, 30–40% diglycerides and 5–9% triglycerides.

3. A pharmaceutical preparation according to claim 1, wherein the antigen, vaccine, or both is a bacterial vaccine, a virus vaccine, a parasite vaccine, or a mixture thereof, which can produce a local or a systemic antibody.

4. A pharmaceutical preparation according to claim 3, wherein the bacterial vaccine is a vaccine for chlamydia, cholera, diphtheria, haemophilus influenzae, leprosy, meningococcal, pertussis, pneumococcal, shigella, tetanus, tuberculosis, or a mixture thereof.

5. A pharmaceutical preparation according to claim 3, wherein the virus vaccine comprises a hepatitis virus, a herpes virus, a human immunodeficiency virus (HIV), an influenza virus, a measles virus, a mumps virus, a parainfluenza virus, a paramyxovirus, a polio virus, a rabies virus, a respiratory syncytial virus, a rhinovirus, a rotavirus, a rubella virus, or a mixture thereof.

6. A pharmaceutical preparation according to claim 3, wherein the parasite vaccine is a vaccine for leishamaniasis, schistosomiasis, trypanosomiasis, or a mixture thereof.

7. A pharmaceutical preparation according to claim 1, further comprising a surfactant, an absorption promoter, a water absorbing polymer, an oil, an emulsion, a liposome, a substance inhibiting enzymatic degradation, an alcohol, an organic solvent, water, a hydrophobic agent, a pH-controlling agent, a preservative, an osmotic pressure controlling agent, a cyclodextrin, a propellant, or a mixture thereof.

8. A pharmaceutical preparation according to claim 1, further comprising an adjuvant or excipient.

9. A pharmaceutical preparation according to claim 1, wherein the composition of the preparation is selected for application to the mucosa of the nose, mouth, eye, ear, vagina or rectum.

10. A method for vaccinating a mammal in need thereof comprising:
   determining a the mammal's suitability for vaccination;
   topically administering to a mucosal membrane of the mammal a vaccine consisting essentially of as an adjuvant or vehicle:
   (a) polyoxyethylene sorbitan monoesters (PS) of the general formula:

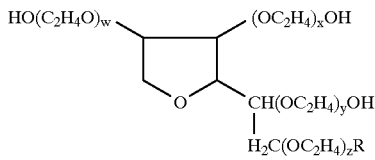

wherein R is laureate, palmitate, stearate or oleate; and each of w, x, y and z is independently 1 or 2; or each of w, x, y, z is independently less than or equal to 17 and the sum of w, x, y and z is 20;
   (b) a mixture of mono-, di-, and triglycerides of a caprylic acid, a capric acid, or both (CCG) having the general formula:

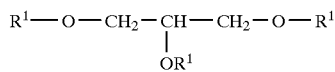

wherein each $R^1$ independently is H or a $C_8$–$C_{10}$ acyl group, provided that at least one $R^1$ is a $C_8$–$C_{10}$ acyl group; and
   (c) water, an aqueous buffer, an antigen, or a combination thereof;
      at respective concentrations of 0.01% to 24% CCG and 0.1% PS to 57.5% PS, each percentage being (v/v) and the preparation containing more PS than CCG and more water or aqueous buffer than oil.

11. The method of claim 10, herein the vaccine is applied to the mucosa of the nose, mouth, eye, ear, vagina or rectum.

12. The method of claim 10, wherein the mixture of mono-, di-, and triglycerides of a caprylic acid, a capric acid, or both contains 1–6% free glycerol, 45–50% monoglycerides, 30–40% diglycerides, and 5–9% triglycerides.

13. A pharmaceutical preparation according to claim 1, wherein a total concentration of CCG and PS is about 45% to about 50%.

14. A pharmaceutical preparation for topical administration of antigens, vaccines, or both to mammals via a mucosal membrane, the preparation consisting essentially of about 18% (v/v) to about 55% (v/v) an antigen, water, an aqueous buffer, or a combination thereof, about 35% (v/v) to about 58% (v/v) polysorbate 20, and about 10% (v/v) to about 24% (v/v) of a mixture of mono-, di-, and triglycerides of a caprylic acid, a capric acid, or both having the general formula:

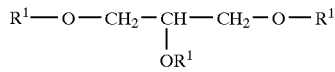

wherein each $R^1$ independently is H or a $C_8$–$C_{10}$ acyl group, provided that at least one $R^1$ is a $C_8C_{10}$ acyl group.

15. A pharmaceutical preparation for topical administration of antigens, vaccines, or both to mammals via a mucosal membrane, the preparation consisting essentially of about 50% (v/v) an antigen, water, an aqueous buffer, or a combination thereof, about 40% (v/v) polysorbate 20, and about 10% (v/v) of a mixture of mono-, di-, and triglycerides of a caprylic acid, a capric acid, or both having the general formula:

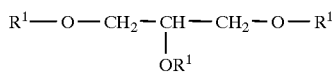

wherein each $R^1$ independently is H or a $C_8$–$C_{10}$ acyl group, provided that at least one $R^1$ is a $C_8$–$C_{10}$ acyl group.

16. A pharmaceutical preparation for topical administration of antigens, vaccines, or both to mammals via a mucosal membrane, the preparation consisting essentially of about 41% (v/v) or about 55% (v/v) an antigen, water, an aqueous buffer, or a combination thereof, about 35% (v/v) polysorbate 20, and about 10% (v/v) or about 24% (v/v) of a mixture of mono-, di-, and triglycerides of a caprylic acid, a capric acid, or both having the general formula:

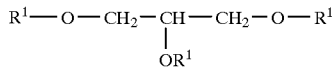

wherein each $R^1$ independently is H or a $C_8$–$C_{10}$ acyl group, provided that at least one $R^1$ is a $C_8$–$C_{10}$ acyl group.

17. A pharmaceutical preparation for topical administration of antigens, vaccines, or both to mammals via a mucosal membrane, the preparation consisting essentially of about 18.5% (v/v) or about 52.5% (v/v) an antigen, water, an aqueous buffer, or a combination thereof, about 57.5% (v/v) polysorbate 20, and about 10% (v/v) or about 24% (v/v) of a mixture of mono-, di-, and triglycerides of a caprylic acid, a capric acid, or both having the general formula:

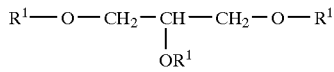

wherein each $R^1$ independently is H or a $C_8$–$C_{10}$ acyl group, provided that at least one $R^1$ is a $C_8$–$C_{10}$ acyl group.

18. A pharmaceutical preparation according to claim 32, 33, or 34, further comprising a surfactant, an absorption promoter, a water absorbing polymer, an oil, an emulsion, a liposome, a substance inhibiting enzymatic degradation, an alcohol, an organic solvent, water, a hydrophobic agent, a pH-controlling agent, a preservative, an osmotic pressure controlling agent, a cyclodextrin, a propellant, or a mixture thereof.

19. A pharmaceutical preparation according to claim 15, 16, or 17, further comprising an adjuvant or excipient.

20. A pharmaceutical preparation for topical administration of antigens, vaccines, or both to mammals via a mucosal membrane, the preparation consisting essentially of:
   (a) a polysorbate 20 (PS);
   (b) a mixture of mono-, di-, and triglycerides of a caprylic acid, a capric acid, or both (CCG) having the general formula:

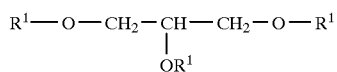
wherein each $R^1$ independently is H or a $C_8$–$C_{10}$ acyl group, provided that at least one $R^1$ is a $C_8$–$C_{10}$ acyl group; and
(c) water, an aqueous buffer, an antigen, or a combination thereof;
wherein, the CCG and PS are present at respective concentrations of 10% CCG and 40% PS, 10% CCG and 35% PS, 10% CCG and 57.5% PS, 24% CCG and 35% PS, or 24% CCG and 57.5% PS; each percentage being (v/v).
* * * * *